United States Patent
Jansson et al.

(10) Patent No.: US 12,285,551 B2
(45) Date of Patent: Apr. 29, 2025

(54) PORT ARRANGEMENT, A PURIFIED WATER PRODUCING APPARATUS COMPRISING THE PORT ARRANGEMENT AND A METHOD FOR PERFORMING PORT CLEANING OF A PURIFIED WATER PRODUCING APPARATUS

(71) Applicants: BAXTER INTERNATIONAL INC., Deerfield, IL (US); BAXTER HEALTHCARE SA, Glattpark (CH)

(72) Inventors: Olof Jansson, Vellinge (SE); Peder Flank, Bjärred (SE)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 0 days.

(21) Appl. No.: 18/598,898

(22) Filed: Mar. 7, 2024

(65) Prior Publication Data

US 2024/0207497 A1  Jun. 27, 2024

Related U.S. Application Data

(62) Division of application No. 16/760,575, filed as application No. PCT/EP2018/079279 on Oct. 25, 2018, now Pat. No. 11,931,495.

(30) Foreign Application Priority Data

Nov. 1, 2017  (SE) .................................... 1751357-3

(51) Int. Cl.
  *A61M 1/16* (2006.01)
  *A61M 39/10* (2006.01)
  (Continued)

(52) U.S. Cl.
  CPC ............ *A61M 1/168* (2013.01); *A61M 39/16* (2013.01); *C02F 1/686* (2013.01);
  (Continued)

(58) Field of Classification Search
  CPC ........ C02F 1/686; C02F 1/68; C02F 2303/14; A61M 1/16; A61M 1/168; A61M 1/3643;
  (Continued)

(56) References Cited

U.S. PATENT DOCUMENTS

| 5,275,724 A | 1/1994 | Bucchianeri et al. |
| 5,591,344 A | 1/1997 | Kenley et al. |

(Continued)

FOREIGN PATENT DOCUMENTS

| CN | 1081623 A | 2/1994 |
| EP | 2862582 A1 | 4/2015 |

(Continued)

OTHER PUBLICATIONS

International Search Report from International Application No. PCT/EP2018/079279 mailed Jan. 28, 2019. 4 Pages.

(Continued)

*Primary Examiner* — Akash K Varma
(74) *Attorney, Agent, or Firm* — K&L Gates LLP

(57) ABSTRACT

A method for performing port cleaning of an apparatus having a casing, a fluid circuit enclosed inside the casing, and a port arrangement. The method includes producing a cleaning fluid with the fluid circuit; passing the cleaning fluid through a first port via a first tube of the first port to a first circumferential space, from the first circumferential space via a bypass channel to a second circumferential space, and thereafter to a second tube of a second port; and passing the cleaning fluid from the second tube to a drain.

15 Claims, 9 Drawing Sheets

(51) Int. Cl.
*A61M 39/16* (2006.01)
*C02F 1/68* (2023.01)

(52) U.S. Cl.
CPC ............... *A61M 2039/1038* (2013.01); *A61M 2039/1083* (2013.01); *A61M 2039/1088* (2013.01); *A61M 2209/10* (2013.01); *C02F 2303/14* (2013.01)

(58) Field of Classification Search
CPC ...... A61M 1/28; A61M 1/154; A61M 1/1686; A61M 1/1682; A61M 39/16; A61M 39/20; A61M 39/10; A61M 39/165; A61M 2039/1083; A61M 2039/1038; A61M 2039/1088; A61M 2039/0009; A61M 2039/0018; A61M 2209/10; B08B 9/032
USPC ........................................................ 210/636
See application file for complete search history.

(56) References Cited

U.S. PATENT DOCUMENTS

| | | |
|---|---|---|
| 5,714,060 A | 2/1998 | Kenley et al. |
| 9,470,341 B2 | 10/2016 | Brehm et al. |
| 9,925,119 B2 | 3/2018 | Takahashi et al. |
| 2011/0064608 A1 | 3/2011 | Lee et al. |
| 2014/0138301 A1 | 5/2014 | Iwahori et al. |
| 2015/0005699 A1* | 1/2015 | Burbank ............... A61M 1/154 604/29 |
| 2015/0021255 A1 | 1/2015 | Takahashi et al. |
| 2015/0151104 A1* | 6/2015 | Ueda ................... A61M 1/1686 137/238 |
| 2015/0359955 A1* | 12/2015 | Wolff .................. A61M 1/1682 210/258 |

FOREIGN PATENT DOCUMENTS

| | | | |
|---|---|---|---|
| EP | 2883566 A1 | 6/2015 | |
| JP | 2003275299 A | 9/2003 | |
| JP | 2013215280 A | 10/2013 | |
| WO | WO-0057935 A1 * | 10/2000 | ........... A61L 2/0023 |
| WO | 2009074588 A1 | 6/2009 | |

OTHER PUBLICATIONS

Written Opinion of the International Searching Authority from International Application No. PCT/EP2018/079279 mailed Jan. 28, 2019. 12 Pages.

* cited by examiner

PORT ARRANGEMENT, A PURIFIED WATER PRODUCING APPARATUS COMPRISING THE PORT ARRANGEMENT AND A METHOD FOR PERFORMING PORT CLEANING OF A PURIFIED WATER PRODUCING APPARATUS

PRIORITY CLAIM

This application claims priority to and claims the benefit as a divisional application of U.S. patent application Ser. No. 16/760,575, filed on Apr. 30, 2020, now U.S. Pat. No. 11,931,495, which is a National Phase of International Application No. PCT/EP2018/079279, filed Oct. 25, 2018, which claims priority to Swedish Application No. 1751357-3, filed Nov. 1, 2017, the entire contents of each of which are incorporated herein by reference and relied upon.

TECHNICAL FIELD

The present disclosure relates to the technical field of ports, and in particular to a port arrangement that regularly has to be cleaned to remove any contaminants. The disclosure further relates to a purified water producing apparatus comprising the port arrangement and a method for performing cleaning of the port arrangement when arranged to the purified water producing apparatus.

BACKGROUND

It has become increasingly common to provide medical care for patients at the patient's home. For patients suffering from renal failure, home therapies with peritoneal dialysis (PD) or hemodialysis (HD) are options that enable the patients to treat themselves at home and reduce the amount of medical centre visits.

Such dialysis treatments require dialysis fluids that typically have been provided ready to use in sealed, sterilized containers. For example, PD treatment requires between 8-20 litres of dialysis fluid per day, 7 days a week, 365 days a year for each patient. Considering the large amount of fluid and the distribution effort to provide each patient with the dialysis fluid, compounding of dialysis fluid at the point of care, e.g. at the patient's home, has been implemented. Concentrates in liquid or dry form are then mixed with water to produce dialysis fluid at the point of care. The concentrates have to be provided to the point of care, but with a much smaller amount than the ready to use dialysis fluids. The concentrates are generally highly concentrated, 10-40× compared to ready to use fluids.

The concentrates should be mixed with water of a very high purity. A water purification apparatus is used to purify water accessible at the point of use, for example tap water. The water purification apparatus is connected to the tap water source and outputs purified water through a product port. A detachable fluid line connects the product port with the dialysis machine, e.g. a cycler or a HD machine, and provides purified water to be used e.g. for mixing with concentrates.

The fluid circuits of the water purification apparatus has to be cleaned and disinfected periodically, to kill any bacteria and remove endotoxins. When manually attaching the line set to the port of the purified water producing apparatus, the port may become contaminated by bacteria from the user's hands.

From U.S. Pat. Nos. 5,714,060A, 5,591,344A it is known to use heated water to disinfect the fluid circuit and connectors of an extracorporeal line set. During this process, connectors of the extracorporeal line set are introduced into dedicated disinfection ports of a disinfection manifold. However, the ports are only used for disinfection of the connectors of the extracorporeal line set and there is no thorough cleaning of the ports themselves.

SUMMARY

It is an objective of the disclosure to alleviate at least some of the drawbacks with the prior art. It is a further objective to provide a port arrangement that enable disinfection of the ports of the arrangement.

These objectives and others are at least partly achieved by the independent claims, and by the embodiments according to the dependent claims.

According to one aspect, the disclosure relates to a port arrangement comprising a fluid module. The fluid module incorporates a first port arranged to receive a first connector, wherein the first port comprises a first tube and a first interior wall concentric with the first tube. The first interior wall provides a first circumferential space around the first tube. The first port further comprises a first seat extending from the first interior wall to form a front end of the first port. The fluid module further incorporates a second port arranged to receive a second connector, wherein the second port comprises a second tube and a second interior wall concentric with the second tube. The second interior wall provides a second circumferential space around the second tube. The second port further comprises a second seat extending from the second interior wall to form a front end of the second port. The fluid module further incorporates a bypass channel connecting the first circumferential space and the circumferential second space. The port arrangement further comprises a door comprising a first seal and a second seal arranged to an inner wall of the door. The door is arranged to be positioned in a closed position against the fluid module, wherein the first seal and the second seal are positioned to the inner wall such that in the closed position the first seal abut against the first seat and the second seal abut against the second seat to thereby seal the first circumferential space and the second circumferential space.

The port arrangement makes it possible to perform a port cleaning that cleans not only the flow channels of the ports, but also the outer sides of the ports, thus an outer side of the first port and an outer side of the second port. The port arrangement enables both the ports to be cleaned in the same run. There is no need for cleaning the outsides of the ports by hand. Further, the bypass channel resides within the fluid module, which enables efficient automatic cleaning of the ports, both inside and outside the connectors of the ports and any connector threads.

According to some embodiments, the bypass channel connect to the first circumferential space at an inner bottom of the circumferential space, and the bypass channel connect to the second circumferential space at an inner bottom of the circumferential space. As the bypass channel is provided in the fluid module, the bypass channel can be provided such that it connects the lower parts of the mentioned circumferential spaces. Thereby it is made sure that a cleaning solution flow across the entire outer sides of the tubes that are exposed to contaminants.

According to some embodiments, wherein the door is in the closed position, the first seal is spaced from an end face of the first tube, and the second seal is spaced from an end face of the second tube. It is here more in detail described that, when the door is closed against the fluid module, the seals are distanced from the end faces of the tubes, such that a cleaning fluid may flow between the provided spaces outside the tubes and the interior of the tubes.

According to some embodiments, the first port is arranged to receive the first connector at the front end of the first port, and to be connected to a product line at a back end of the first port. The second port is arranged to receive the second connector at the front end of the second port, and to be connected to a drain line at a back end of the second port. Thus, the first port may be used to connect a product line to a first connector, and to pass purified water from the product line to the first connector, and the second port may be used to connect a second connector to a drain line, and to pass drain fluid from the second connector to the drain line.

According to some embodiments, the first port and the second port are designed as conical fittings of Luer type. Thus, the ports may include standard Luer type connectors that have been modified such that their outer sides can be cleaned during a port cleaning. The Luer type may be provided with locking thread.

According to some embodiments, the second tube has a threaded outer side. The second port may thus incorporate a female conical fitting of Luer type.

According to some embodiments, the first interior wall is threaded. The first port may thus incorporate a male conical fitting of Luer type.

According to some embodiments, the bypass channel includes a main bore, a first circumferential gap around the first tube connecting to the first circumferential space, a second circumferential gap around the second tube connecting to the second space, and where the main bore connects the first circumferential gap and the second circumferential gap. Thus, the bypass channel is made up of several circumferential gaps that allow cleaning fluid to flow across the external sides of the tubes during cleaning.

According to some embodiments, the bypass channel includes a third circumferential gap connecting to the second space and to the main bore. Thereby cleaning fluid is allowed to flow in a larger space that promotes a total cleaning.

According to some embodiments, the port arrangement comprises a sensor arrangement configured to detect whether the door is in the closed position or not, and to generate a door position signal indicating the position of the door. Thereby it will be known when the seals are closing the spaces around the ports against the outside such that a port cleaning can be performed.

According to some embodiments, the port arrangement comprises a spring-loaded latch assembly for locking the door to the fluid module. Thereby the door can be held closed to the fluid module during cleaning.

According to some embodiments, the door further comprises a spring arrangement with a spring arranged between a spring seat of the door and the second seal. The second seal is being biased by the spring against an incision of an inner wall of the door with a predetermined spring force, the second seal being movable a distance Δd against the spring seat by overcoming the spring force. Thereby the door can be held distanced from the fluid module when it is not closed, such that the sensing arrangement will not erroneously sense report that the door is closed when it is not properly closed.

According to some embodiments, the first seal and/or the second seal is arranged with an irregular surface to promote distribution of fluid.

According to a second aspect, the disclosure relates to a purified water producing apparatus comprising a casing, a fluid circuit enclosed inside the casing and arranged to produce a flow of purified water from a source of water and to transport used fluid to a drain, and a port arrangement as described herein. The port arrangement is arranged to the casing such that the door, the front end of the first port and the front end of the second port are accessible from the outside of the water producing apparatus to allow fluid connection of the first connector and the second connector, and the first port and the second port are fluidly connected to the fluid circuit at respective back ends of the ports. Thus, the purified water producing apparatus is provided with a port arrangement that allows thorough cleaning of the ports. Thereby any bacteria of the ports may be mitigated, and the purity level of the purified water flowing through the first port may be maintained.

According to some embodiments, the water producing apparatus comprises a control unit arranged to receive a door position signal indicating a position of the door. The water producing apparatus is further arranged to control a flow of cleaning fluid to the port arrangement based on the position of the door. For example, if someone accidently opens the door, the flow of cleaning fluid to the port arrangement will be stopped. The cleaning fluid may be purified water, heated purified water, purified water comprising a cleaning agent, or heated purified water comprising a cleaning agent.

According to some embodiments, wherein the water producing apparatus is arranged to direct cleaning fluid to the back end of the first port upon the door position signal indicates that the door is in a closed position. The cleaning fluid then enters the first tube and flows into the first space of the first port, thereafter via the bypass channel to the second space and into the second tube, where after the cleaning fluid leaves the second port via the back end of the second port and is further transported to a drain via the fluid circuit. Thus, if the door is closed, cleaning fluid is allowed to flow through the port arrangement such that a cleaning of the ports can be performed.

According to some embodiments, the fluid circuit comprises a heating device arranged to heat the cleaning fluid to a temperature meeting a cleaning criterion for the first port and the second port. Thus, the cleaning fluid may be heated such that a disinfection of the ports may be performed.

According to a third aspect, the disclosure relates to a method for performing port cleaning of a water producing apparatus. The method comprising producing a cleaning fluid with the fluid circuit, passing the cleaning fluid through the first port via the first tube to the first circumferential space, from the first circumferential space via the bypass channel to the second circumferential space, and thereafter to the second tube and passing the cleaning fluid from the second tube to the drain. By the method, a thorough cleaning of the ports can be performed.

According to some embodiments, the method comprises passing the cleaning fluid during a certain time period meeting a cleaning criterion for the first port and the second port. The time period may be set beforehand, or determined during performance of the method based on the composition of the cleaning fluid and/or the temperature of the cleaning fluid.

According to some embodiments, the method comprises receiving a signal indicating that the door is closed, before performing the passing step. Thus, the door has to be properly closed before the port cleaning is performed.

According to some embodiments, the producing comprises producing a heated cleaning fluid. Thereby a heat disinfection of the ports may be performed by using the heated cleaning fluid for the port cleaning.

According to a fourth aspect, the disclosure relates to a computer program comprising instructions which, when the program is executed by a control unit, cause the control unit and a thereto associated water producing apparatus to carry out the method as described herein.

A computer-readable medium comprising instructions which, when executed by a control unit, cause the control unit and a thereto associated water producing apparatus to carry out the method.

DETAILED DESCRIPTION

In the following a port arrangement will be described, that enable the ports of the port arrangement to be cleaned e.g. disinfected by a cleaning fluid such that also external parts of the ports are cleaned and/or disinfected. The cleaning fluid may be purified water, heated purified water, purified water with a cleaning agent or heated purified water with a cleaning agent. The cleaning agent may be an bacterial growth inhibiting agent, e.g. a physiologically safe acid, such as citric acid, citrate, lactic acid, acetic acid, hydrochlorid acid, a combination or a derivative thereof. The port arrangement includes a door and a fluid module including the ports. When the door is closed against the fluid module, external sides of the ports are part of the disinfection paths of the ports, and the respective disinfection path of the ports are connected via a bypass channel. Cleaning fluid can then be passed one-way through the fluid module and clean the interior and external sides of the ports in the same run. Thereby, also the external sides of the ports, which may be contaminated from touching by hands of the user etc., are cleaned and bacterial growth is combated.

In the following, exemplary embodiments of the port arrangement will be explained, with reference to the figures. The port arrangement may be implemented to various apparatuses that are capable of providing a flow of cleaning fluid, but will in the following be exemplified as implemented to an apparatus capable of producing purified water.

Figure 1:
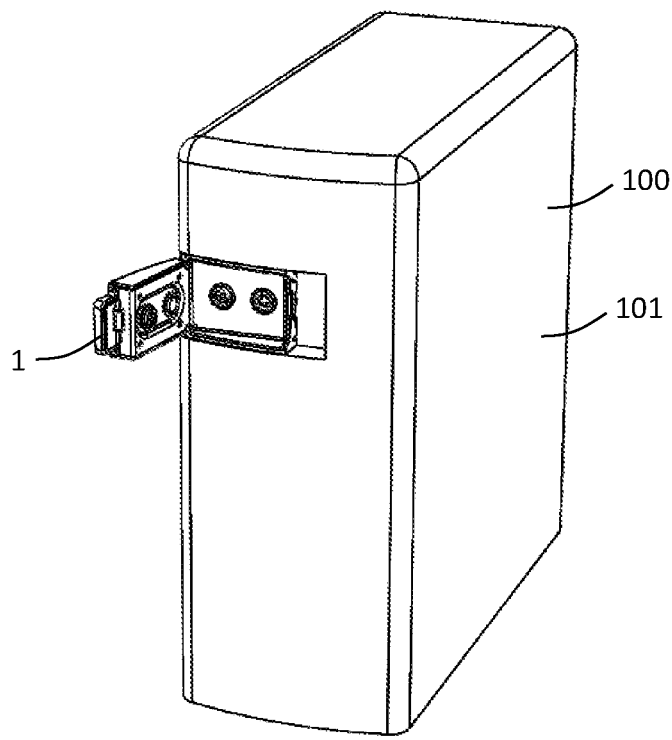
FIG. 1 illustrates a purified water apparatus according to some embodiments.

In FIG. 1 a water purification apparatus 100 is illustrated. The water purification apparatus 100 is provided with a casing 101 enclosing a fluid circuit of the water purification apparatus 100. A port arrangement 1 is arranged to the casing 101 for connection of connectors of a fluid line set (not shown) to the fluid circuit.

Figure 2:
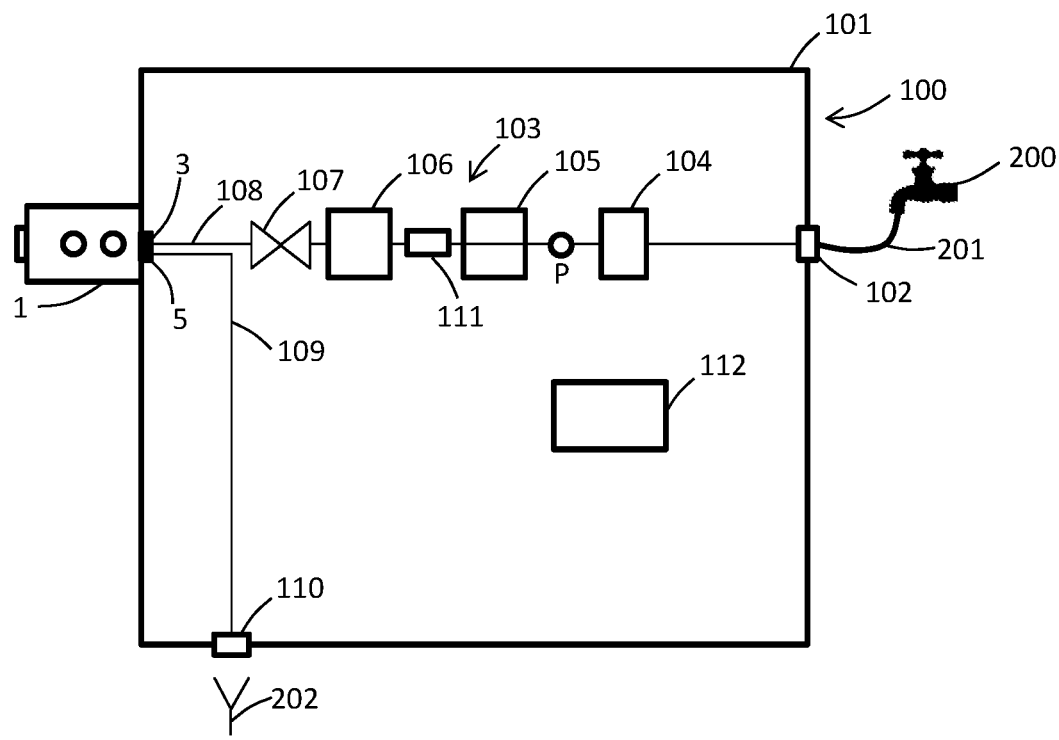
FIG. 2 illustrates the interior fluid circuit of the purified water apparatus of FIG. 1 according to some embodiments.

FIG. 2 schematically illustrates main components of the water purification apparatus 100. The water purification apparatus 100 comprises an inlet port 102, a fluid circuit 103, the port arrangement 1, a drain port 110 and a control unit 112. The fluid circuit 103 is enclosed inside the casing 101 and is arranged to produce a flow of purified water from a source of water 200 connected via the inlet port 102, and to transport used fluid to a drain 202 via the drain port 110. The inlet port 102 is here connected to the source of water 200 being a water tap with a connecting line 201. The fluid circuit 103 comprises a pre-filter unit 104, a Reverse Osmosis Unit (RO Unit) 105 and a post-treatment unit 106, all fitted to a product line 108. The product line 108 is connected to the inlet port 102 at one end, and to a first port 3 of the port arrangement 1 at the other end. It should be understood that the product line 108 is here conceptually described as one line, but could include several lines interconnected by the units etc. described as fitted to the product line 108. The pre-filter unit 104 is arranged to receive (unfiltered) water from the water tap, and is arranged to produce filtered water. The pre-filter unit 104 may include a particle filter and a bed of activated carbon. The RO unit 105 is arranged downstream the pre-filter unit 104 to receive the filtered water from the post-treatment unit 106. The RO unit 105 comprises a semi-permeable membrane, and outputs permeate water. The post-treatment unit 106 is arranged downstream the RO unit 105 and is arranged to receive the permeate water from the RO unit 105. The post-treatment unit 106 further treats the permeate water and produces purified water. The post-treatment unit may include a polisher such as an Electrodeionization device (EDI device).

A pump P is arranged upstream the RO unit 105 to provide a pressurized flow of water to the RO unit 105. A heating device 111 is arranged downstream the RO unit 105, but upstream the post-treatment unit 106, to heat the permeate water to a certain temperature between 70° C. and 95° C. A valve device 107 is arranged at the product line 108 to regulate the flow in the product line 108, e.g. downstream the post-treatment unit 106. Alternatively, the valve device 107 may be arranged to a recirculation line (not shown) between a point downstream the heating device 111 but upstream the post-treatment unit 106, and a point upstream the RO unit 105. The pump P, the heating device 111 and the valve device 107 are arranged to be controlled by a control unit 112 of the water purification apparatus 100. The control unit 112 is arranged to control the pump P, the heating device 111 and the valve device 107, by sending respective signals to the same. Specifically, the control unit 112 is arranged to control the pump to pump water with a certain flow rate, to control the heating device 111 to heat permeate water to a certain temperature, and to control the valve device 107 to stop or start a flow of fluid in the product line 108 upstream the post-treatment unit 106. The heating device 111 is further arranged to heat the purified water to a temperature meeting a cleaning criterion, e.g. a disinfection criterion, for the first port 3 and the second port 5. The temperature of the purified water may be measured by a temperature sensor (not shown) arranged to the product line 108 downstream the heating device 111. The sensed temperature is sent to the control unit 112 whereupon the control unit 112 controls the heating device 111 based on the measured temperature such that the temperature meets the cleaning criterion. The cleaning criterion may include temperature and/or time duration for the cleaning.

The fluid circuit 103 further includes a drain line 109 connected between a second port 5 of the port arrangement 1 and the drain port 110. The drain port 110 outputs drain water, e.g. used dialysis fluid or used cleaning fluid, via the second port 5 to the drain 202.

Figure 3:
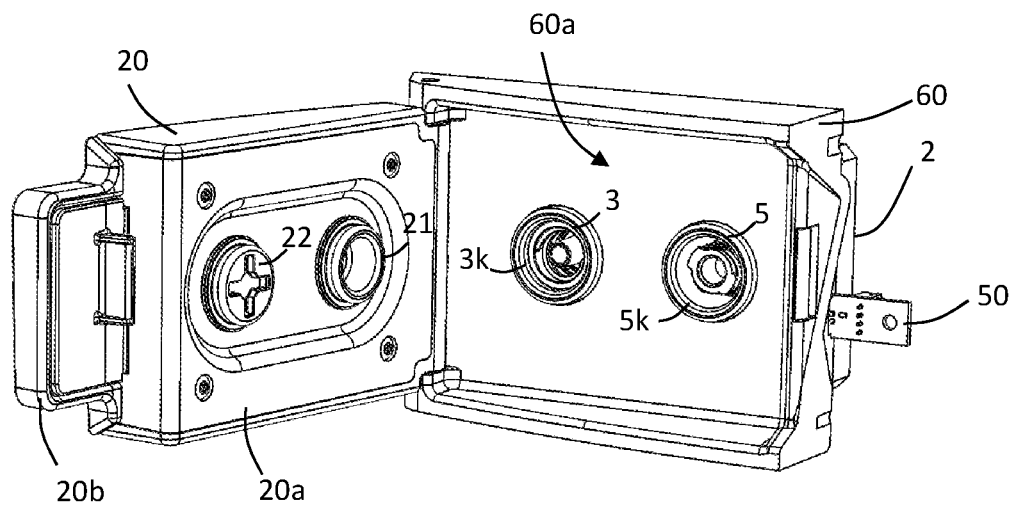
FIG. 3 illustrates a front view of a port arrangement according to some embodiments.

FIG. 3 illustrates an isolated front view of the port arrangement 1. The port arrangement 1 comprises a fluid module 2 and a door 20. The fluid module 2 is made of a heat resistant material that does not release toxic substances. For example, the fluid module 2 is made of polypropylene. The door 20 comprises an integrated first body part 20a and second body part 20b. The second body part 20b is a smaller extension of the first body part 20a. The first body part 20a comprises a first seal 21 and a second seal 22. The door 20 is attached to the fluid module 2 with a hinge 24 (FIG. 15), and can be closed against the fluid module 2 into a closed position. The port arrangement 1 further comprises a port casing 60 or "port house" holding and partly enclosing the fluid module 2, and provides an attachment for the fluid module 2 to the casing 101 (FIG. 1). The port arrangement 1 further comprises a sensor arrangement 50, e.g. including a Hall-sensor, connected to the port casing 60 or fluid module 2, which is configured to sense the proximity of a magnet (not shown) positioned in the door 20, or more precisely in the first body part 20a. The sensor arrangement 50 is configured to detect whether the door 20 is in the closed position or not, and to generate a door position signal indicating the position of the door 20. The door position signal thus indicates whether the door 20 is closed or not. The sensor arrangement 50 is arranged to send the door position signal to the control unit 112. If the signal indicates that the door 20 is closed, the control unit 112 is arranged to control the valve unit 107 to open the flow in the product line 108 to the first port 3. If the signal indicates that the door 20 is open, the control unit 112 is arranged to control the valve unit 107 to close the flow in the product line 108 to the first port 3. In other words, the water producing apparatus 100 is arranged to control the flow of cleaning fluid, e.g. purified water, to the port arrangement 1 based on the position of the door 20.

The fluid module 2 further comprises the first port 3 and the second port 5. The port casing 60 is provided with a casing wall 60a with two through-holes. The first port 3 and the second port 5 are aligned with the through-holes, such that a front end 3k of the first port 3 is accessible through one of the holes, and a front end 5k of the second port 5 is accessible through the other hole, and such that connectors can be connected to the respective ports through the holes. The first fluid port 3 is designed such that a first connector 4 (FIG. 10) can be fluidly connected to the first fluid port 3 at the front end 3k. In other words, the first fluid port 3 is arranged to receive the first connector 4 at the front end 3k. The second fluid port 5 is designed such that a second connector 6 (FIG. 10) can be fluidly connected to the second fluid port 5 at the front end 5k. In other words, the second fluid port 5 is arranged to receive the second connector 6 at the front end 5k. Parts of the first port 3 and the second port 5 are recessed into the casing wall 60a in the through-holes of the casing wall 60a.

Figure 4:
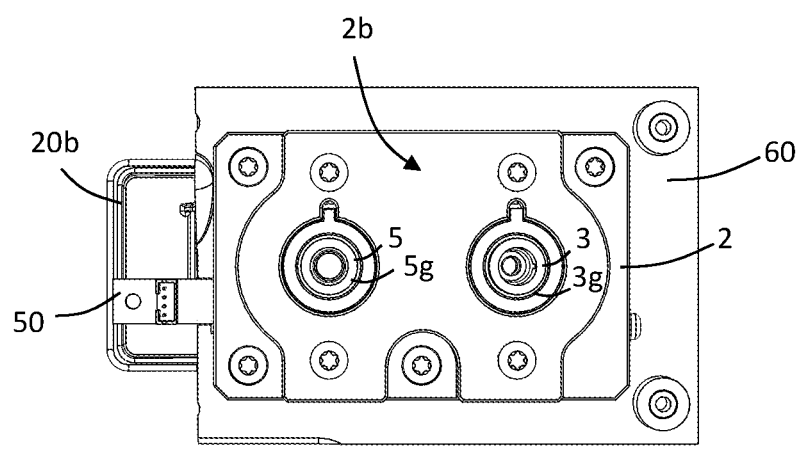
FIG. 4 illustrates a back view of the port arrangement of FIG. 3 according to some embodiments.

FIG. 4 illustrates a back view of the port arrangement 1 of FIG. 1. The back of the port arrangement 1 is, when arranged to the wall of the casing 101, facing the interior of the water purification apparatus 100. The fluid module 2 comprises a back side 2c exhibiting a back end 3g of the first fluid port 3, and a back end 5g of the second fluid port 5. The first fluid port 3 is designed to be fluidly connected to the product line 108 (FIG. 2) at the back end 3g. The second fluid port 5 is designed to be fluidly connected to the drain line 109 (FIG. 2) at the back end 5g.

With reference to FIGS. 1-4, the port arrangement 1 is arranged to the casing 101 such that the door 20, the front end 3k of the first port 3 and the front end 5k of the second port 5 are accessible from the outside of the water producing apparatus 100 to allow fluid connection of the first connector 4 and the second connector 6. Then the first port 3 and the second port 5 are fluidly connected to the fluid circuit 103 at respective back ends 3g, 5g of the ports 3, 5.

Figure 5:
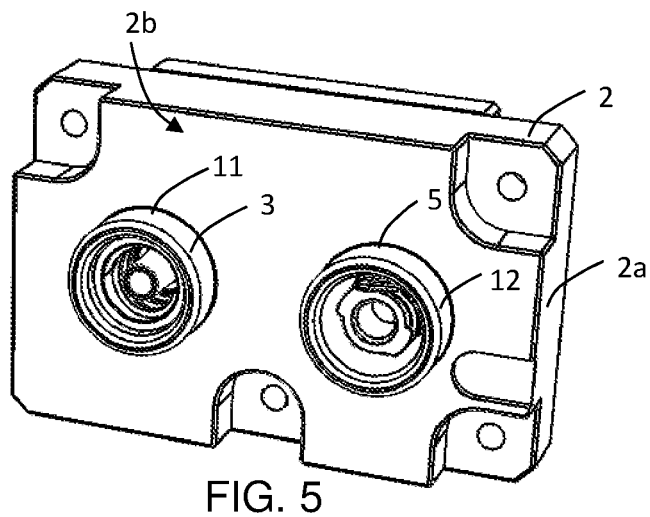
FIG. 5 illustrates a front view of a fluid module of the port arrangement according to some embodiments.

FIG. 5 illustrates the fluid module 2 in isolation from a front view. The fluid module 1 comprises a body 2a with front side 2b. An outer circumferential wall 11 of the first port 3 projects perpendicularly from the front side 2b with a distance d1. An outer circumferential wall 12 of the second port 5 projects perpendicularly from the front side 2b with a distance d2.

Figure 6:
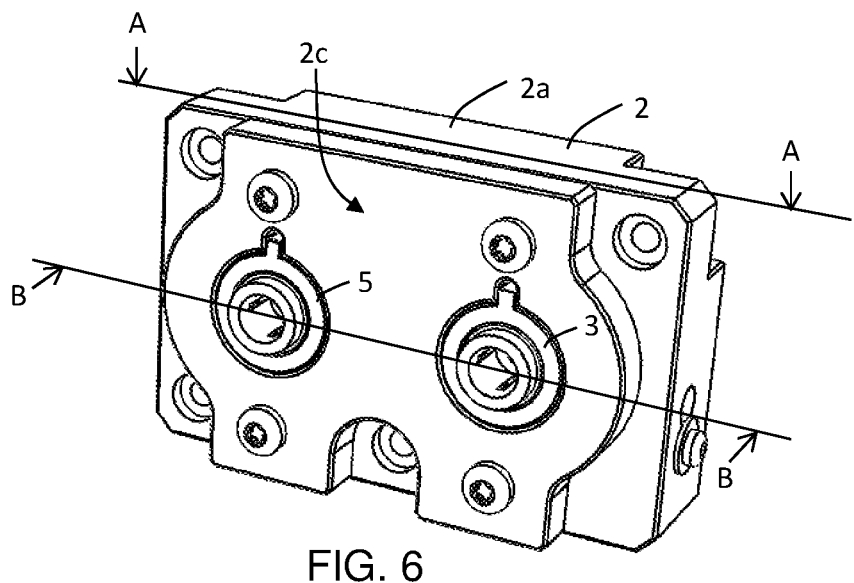
FIG. 6 illustrates a back view of the fluid module of FIG. 5 according to some embodiments.

FIG. 6 illustrates the fluid module 2 from a back view. The body 2a comprises a back side 2c, positioned on the opposite side of the body 2a with regards to the front side 2b. The body 2a is here made up of two body pieces for ease of construction, but may be made in one piece, or more than two pieces.

Figure 7:
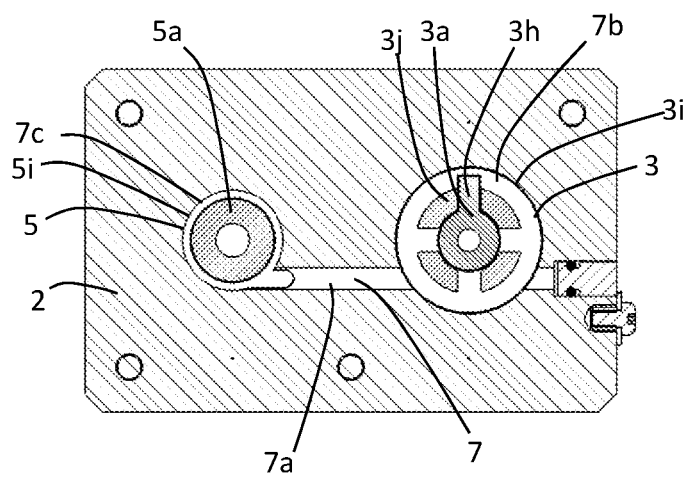
FIG. 7 illustrates a vertical cross section in the plane A-A of FIG. 6.

FIG. 7 illustrates a cross-section of the fluid module 2 along a plane A-A of FIG. 6. As seen from the cross-section, the first port 3 and the second port 5 are fluidly connected with a bypass channel 7. The fluid module 2 is crossed by a first bore 3i with a varying first diameter and a second bore 5i with a varying second diameter. The first bore 3i and the second bore 5i are circular passages perpendicular to the front side 2b of the fluid module 2. These bores are thus through-holes. The first bore 3i accommodates a first tube 3a of the first port 3. The second bore 5i accommodates a second tube 5a of the second port 5. The first port 3 further comprises a keying means 3h in the first tube 3a arranged to hold the first tube 3a in place in a certain orientation against a socket 3j inside the first bore 3i. Between the inner side of the first bore 3i and the outer side 3e of the first tube 3a, a first circumferential gap 7b is provided. Between the inner side of the second bore 5i and the outer side 5e of the second tube 5a, a second circumferential gap 7c is provided. A main bore 7a of the bypass channel 7 fluidly connects the first circumferential gap 7b and the second circumferential gap 7c at a lower part of the first circumferential gap 7b and the second circumferential gap 7c. Thereby, the risk that any fluid will be left in any space below the bypass channel 7 is reduced. The bypass channel 7 is arranged to fluidly connect the first circumferential space 3c and the second circumferential space 5c at lower or lowermost parts thereof, when the fluid module 2 is in an operating position in the wall of the casing 101 (see FIGS. 1-2 and 10-13). Thereby all spaces will be accessed during a cleaning. The main bore 7a is arranged parallel to the front side 2b of the fluid module 2.

Figure 8:
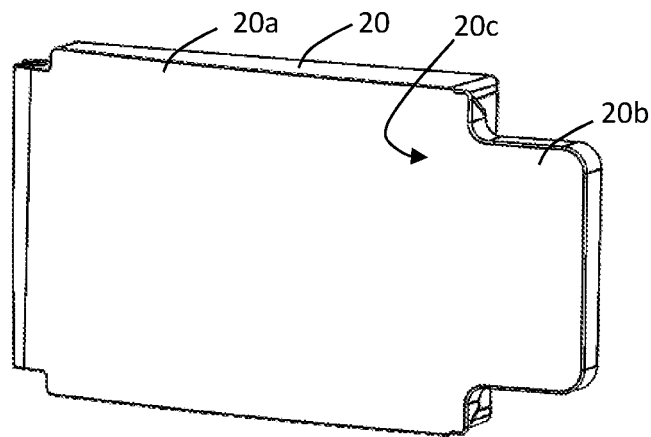
FIG. 8 illustrates a front view of a door of the port arrangement according to some embodiments.
Figure 9:
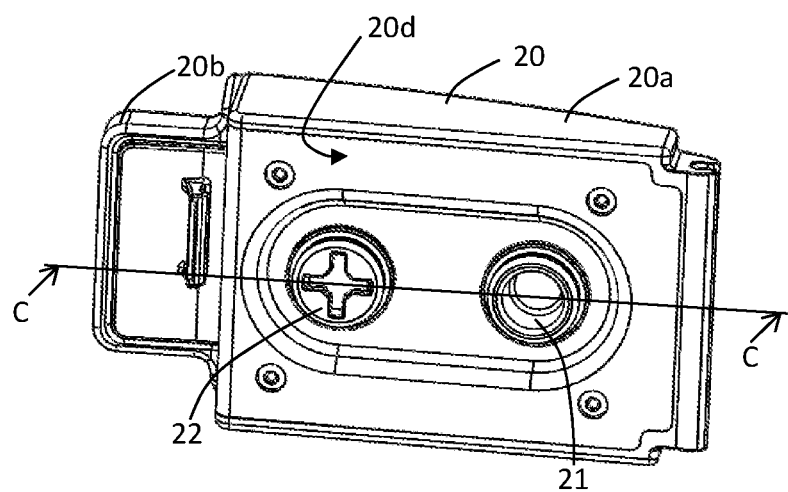
FIG. 9 illustrates a back view of the door in FIG. 8 according to some embodiments.

FIG. 8 illustrates a front view of the door 20. The door 20 comprises a front side 20c extending over both the first part 20a and the second part 20b. FIG. 9 illustrates a back view of the door 20. The door 20 comprises an inner wall 20d, positioned on the opposite side of the door 20 of the front side 20c. The door 20 is provided with a first seal 21 and a second seal 22. As can be seen, the first seal 21 is hollow, and the second seal 22 is provided with a cross-like recess.

Figure 10:
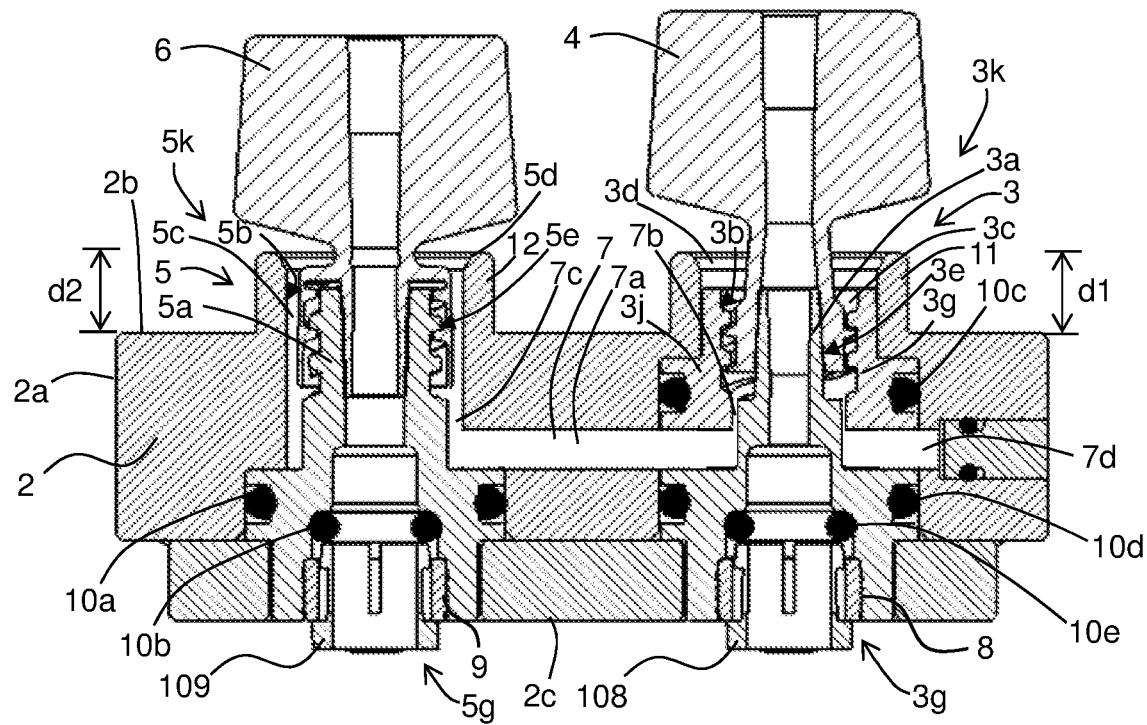
FIG. 10 illustrates a horizontal cross section along the plane B-B of the fluid module in FIG. 6, when the ports are attached to corresponding connectors of the fluid line set.

FIG. 10 illustrates a cross-section of the fluid module 2 shown in FIG. 6, along a plane defined by B-B. The bypass channel 7 has been moved towards the observer of FIG. 10 in order to make the bypass channel 7 visible in the figure. As mentioned, the fluid module 2 comprises a body 2a with a front side 2b and a back side 2c. The body 2a is made of several separate body parts that are assembled together. The body 2a comprises a first bore 3i (FIG. 7) and a second bore 5i (FIG. 7). The first port 3 comprises a first tube 3a, accommodated in the first bore 3i. A socket 3j is arranged aligned with the inner wall of the first bore 3i. The socket 3j defines a first interior wall 3b concentric with the first tube 3a. The first tube 3a is arranged inside the socket 3j. The first interior wall 3b provides a first circumferential space 3c around the first tube 3a. In FIG. 10 a first connector 4 has been connected to the first port 3. The first connector 4 is a female connector including a tube with a threaded outer side, for example a female conical fitting of Luer type. The first circumferential space 3c has such size that it can accommodate the threaded tube of the female connector. Thus, the first interior wall 3b has a diameter greater to an outer diameter of the first connector 4. The first interior wall 3b is correspondingly threaded. The first tube 3a and the first interior wall 3b makes up, or provides, a male connector of Luer type, for example a male conical fitting of Luer type. The conical fittings herein may have a 6% taper. The threads of the threaded tube of the female connector 4 engage with the threads of the first interior wall 3b to create a fluid tight connection. The first tube 3a extends in the first bore 3i to the back end 3g of the first port 3 and to the back side 2c of the fluid module where the first tube 3a is connected with the product line 108 with a first bond 8. The fluid tightness of the connection may be secured with a gasket 10e between the product line 108 and the tube 3a. The first bond 8 includes means to secure the product line 108 to the inside of the first tube 3a.

The first port 3 further comprises a first seat or shoulder 3d in the body 2, extending from the first interior wall 3b to form a front end of the first port 3. The first seat 3d is further the front end of the outer circumferential wall 11 of the first port 3. The first seat 3d is connected to the inner wall of the socket 3j via an outer face of the socket 3j. The first seat 3d thus comprises also the outer face of the socket 3j.

The second port 5 comprises a second tube 5a, accommodated in the second circumferential bore 5i. The second tube 5a is thus arranged inside the bore 5i. The bore 5i defines a second interior wall 5b concentric with the second tube 5a. The second interior wall 5b provides a second circumferential space 5c around the second tube 5c. In FIG. 10 a second connector 6 has been connected to the second port 5. The second connector 6 is a male connector with a tube and an outer collar with an interior thread, for example a male conical fitting of Luer type. The second circumferential space 5c has such size that it can accommodate the threaded collar of the male connector 6. Thus, the second interior wall 5b has a diameter greater than an outer diameter of the second connector 6. The outer side 5e of the second tube 5a is correspondingly threaded. The second tube 5a makes up, or provides, a female connector of Luer type, for example a female conical fitting of Luer type. The conical fittings herein may have a 6% taper. The threads of the threaded collar of the male connector 6 engage with the threads of the second tube 5a to create a fluid tight connection. The second tube 5a extends in the bore 5i to the back end 5g of the second port 5 and to the back side 2c of the fluid module. There, the second tube 5a is connected with the drain line 109 with a second bond 9. The fluid tightness of the connection may be secured with a gasket 10b between the drain line 109 and the tube 5a. The second bond 9 includes means to secure the drain line 109 to the inside of the second tube 5a.

A connector of Luer type may be designed according to ISO 594-1:1986, ISO 594-2:1998, ISO 80369-1:2010, ISO/DIS 80369-7:2013, ISO 8637:2014 or ISO 8638:2014.

The second port 5 further comprises a second seat or shoulder 5d in the body 2, extending from the second interior wall 5b to form a front end of the second port 5. The second seat 5d is further the front end of the outer circumferential wall 12 of the second port 5.

The fluid module 2 further comprises the bypass channel 7. The bypass channel 7 fluidly connects the first circumferential space 3c and the circumferential second space 5c. The bypass channel 7 includes a main bore 7a, a first circumferential gap 7b around the first tube 3a connecting to the first circumferential space 3c, a second circumferential gap 7c around the second tube 5a connecting to the second space 5c. The main bore 7a connects the first circumferential gap 7b and the second circumferential gap 7d. The first circumferential gap 7b is a space between the first bore 3i and the first tube 3a, that opens up between the first circumferential space 3c and the main bore 7a. The second circumferential gap 7c is a space between the second bore 5i and the second tube 5a, that opens up between the second circumferential space 5c and the main bore 7a. The bypass channel 7 also includes a third circumferential gap 7d connecting to the second circumferential space 5c and to the main bore 7a. The third circumferential gap 7d provides a large space where fluid can flow.

When the first connector 4 is connected to the first port 3, and the second connector 6 is connected to the second port 5, as illustrated in FIG. 10, no fluid flowing in the tubes of the ports can reach the first space 3c, the second circumferential space 5c or the bypass channel 7. Thus, the flow during normal operation is only directed through the channels of the ports 3, 5.

Figure 11:
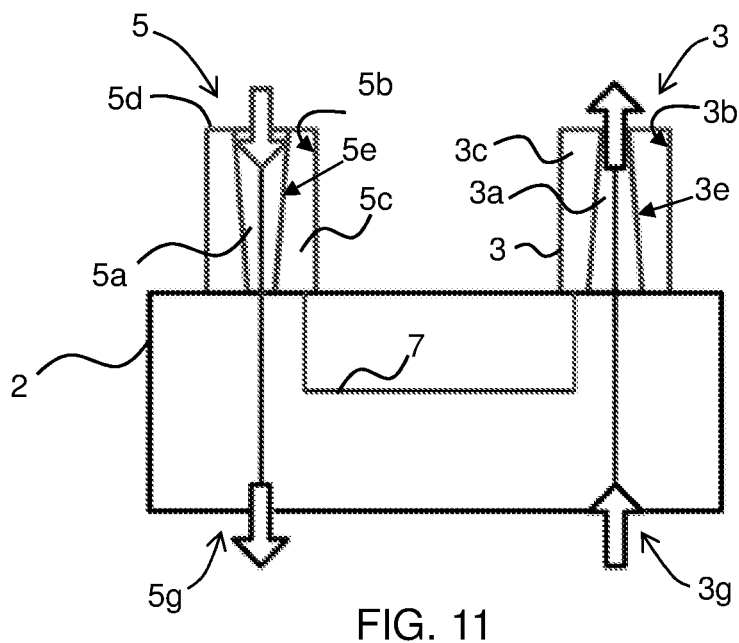
FIG. 11 illustrates a schematic of the flows across the fluid module during production of purified water and removal of drain water.

FIG. 11 schematically illustrates a flow scheme of the flows in FIG. 10 in normal operation, i.e. when the fluid module 2 is arranged to an apparatus for passing purified water through the first port 3, and to receive drain fluid through the second port 5. For ease of illustration, the apparatus, the connectors, the port casing 60 and the door 20 are not shown in the figure. The arrows illustrate the flows through the ports 3, 5. As illustrated by the arrows, in operation, purified water flows through the first port 3 from the back end of the first port 3 and out from the front end of the first port 3. A drain fluid flows through the second port 5 from the front end of the second port 5 and out from the back end of the second port 5. No fluid is conducted through the bypass channel 7.

Figure 12:
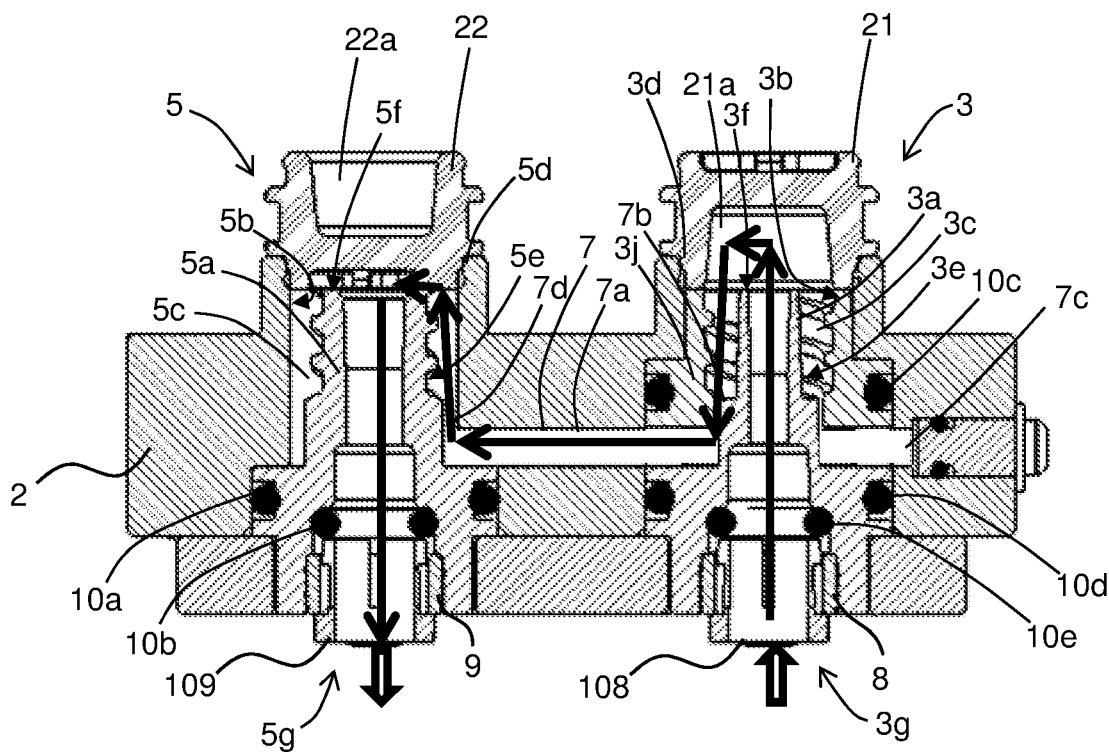
FIG. 12 illustrates a horizontal cross section in the plane B-B of the fluid module in FIG. 6 with a disinfection fluid path schematically depicted, when the ports are sealed.

In FIG. 12 the first connector 4 and the second connector 6 have been removed, and the door 20 has been closed against the fluid module 2 to a closed position. Thus, the fluid module 2 is sealed by the first seal 21 and the second seal 22 of the door 20. Reference is made to FIG. 10 for description of the fluid module 2. For ease of illustration, the door 20 itself is not shown, only the first seal 21 and the second seal 22 are visible.

In the closed position, the first seal 21 abuts against the first seat 3d and the second seal 22 abuts against the second seat 5d to thereby seal the first circumferential space 3c and the second circumferential space 5c. More in detail, an outer flange or collar of the first seal 21 abut against the upper end of the first seat 3d and an outer face of the first seal 21 abut against the outer face of the socket 3j. Also, an outer flange or collar of the second seal 22 abuts against the upper end of the second seat 5d. The seals 21, 22 are thus partly inserted into the bores 3i, 5i, respectively. The outer flange of respective seal 21, 22 prohibit further advancement of the seal 21, 22 into the respective bore 3i, 5i. The first tube 3a defines an end face 3f in the front end of the first port 3. The second tube 5a defines an end face 5f in the front end of the second port 5. A side of the first seal 21 exhibiting a space 21a faces the end face 3f of the first tube 3a. A side of the second seal 22 exhibiting an irregular surface faces the end face 5f of the second tube 5a. Further, in this closed position, the first seal 21 is spaced from the end face 3f of the first tube 3a, and the second seal 22 is spaced from the end face 5f of the second tube 5a. Thereby, fluid (illustrated by the large arrows) is allowed to flow from the back end 3g of the first port 3 into the first tube 3a and further into the first circumferential space 3c of the first port 3, thereafter via the bypass channel 7 to the second circumferential space 5c and into the second tube 5c, whereafter the fluid leaves the second port 5 via the back end 5g of the second port 5. The seals 21, 22 are preventing the cleaning fluid from leaking and allows the fluid to flow between the tube and the internal side of the first port 3. The seals 21, 22 also allow the fluid to drain through the center of the second port 5.

The bypass channel 7 connects to the first circumferential space 3c at an inner bottom or end of the circumferential space 3c. The bypass channel 7 further connects to the second circumferential space 5c at an inner bottom or end of the circumferential space 5c. Thereby, it is assured that the flow of cleaning fluid will reach all the outer parts of the ports 3, 5, also the most proximal external parts of the ports 3, 5, which the connectors 4, 6 will reach or have reached when they are connected to the ports 3, 5.

Figure 13:
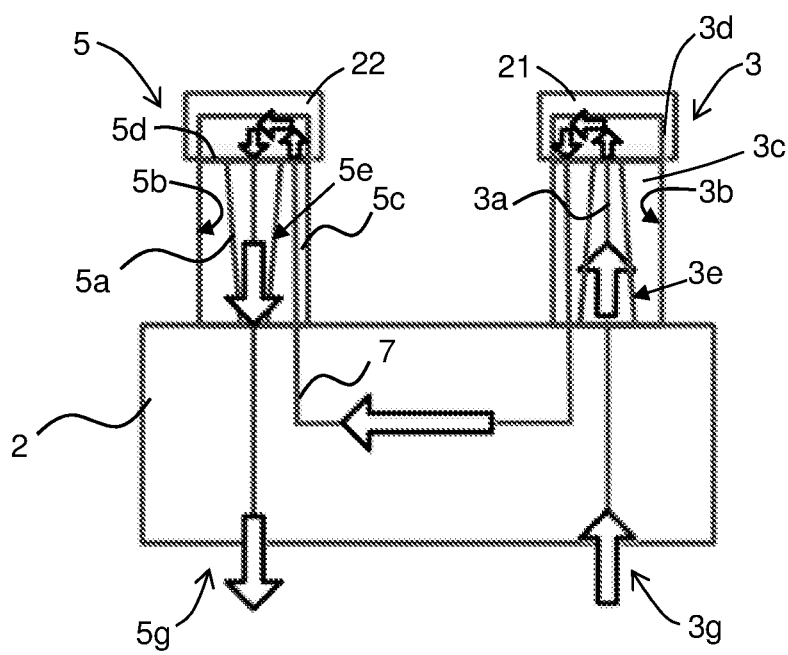
FIG. 13 illustrates a schematic of the flows across the fluid module during disinfection of the fluid module, when the ports are sealed.

FIG. 13 schematically illustrates a flow scheme of the flows in FIG. 12. For ease of illustration, the apparatus, the connectors, the port casing 60 and the door 20 are not shown in the figure, only the seals 21, 22 are shown. The arrows illustrate the flows through the ports 3, 5 and the bypass channel 7. The flow is the same as has been explained in connection with FIG. 12. More in detail, with reference to both FIGS. 12 and 13, the water producing apparatus 100 is arranged to direct cleaning fluid to the back end 3g of the first port 3 when the door position signal indicates that the door 20 is in a closed position. The cleaning fluid then enters the first tube 3a and flows into the first circumferential space 3c of the first port 3, thereafter via the bypass channel 7 to the second space 5c and into the second tube 5c, where after the cleaning fluid leaves the second port 5 via the back end 5g of the second port 5, and is further transported to the drain 201 via the drain line 109 of the fluid circuit 103.

Figure 14:
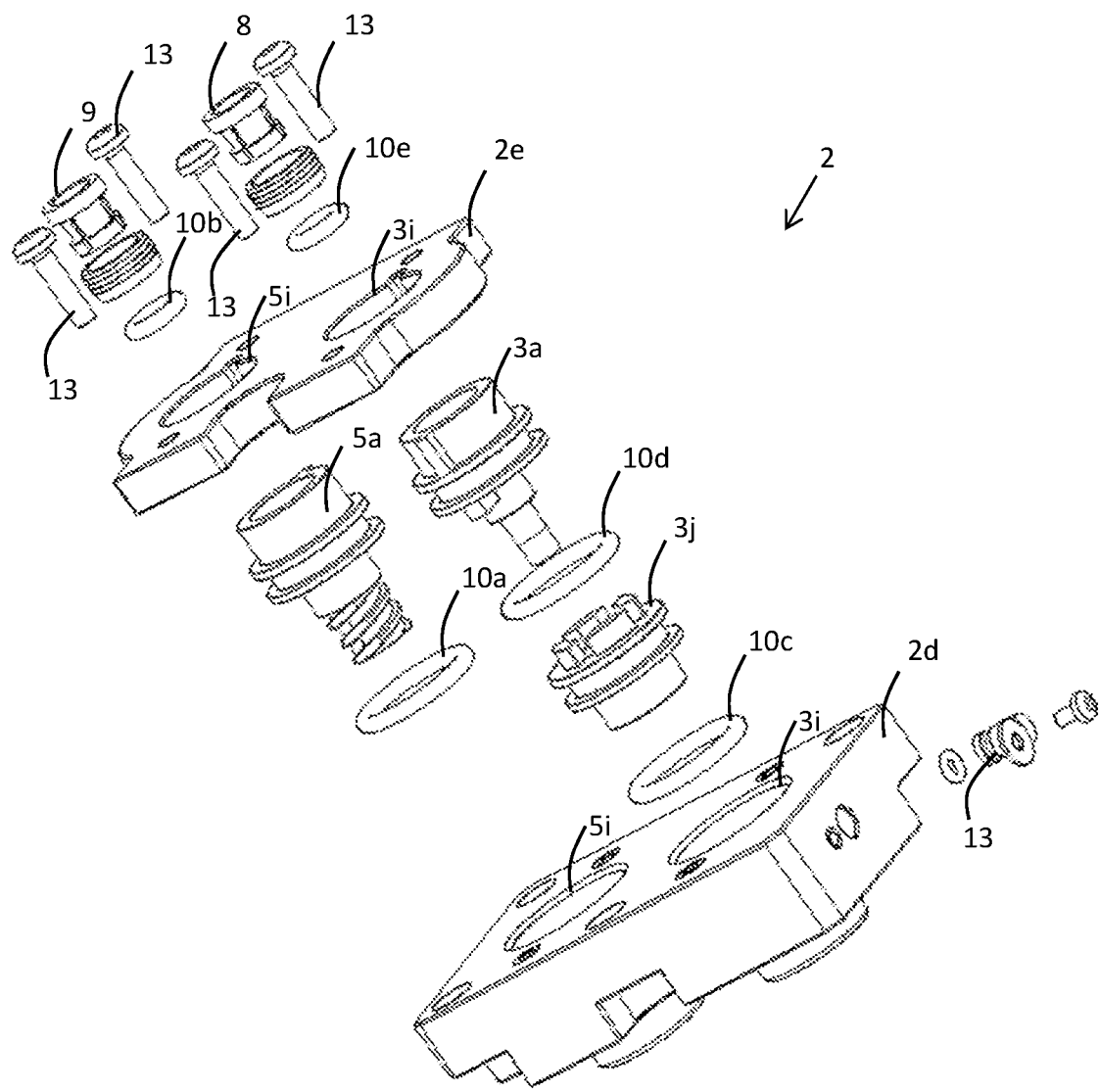
FIG. 14 illustrates an exploded view of the fluid module in FIG. 6.

FIG. 14 illustrates the fluid module 2 in an exploded view. The fluid module 2 comprises a body made up of a first body piece 2d and a second body piece 2e, that are secure to each other by means of screw joints, i.e. screws 13 and corresponding bolts (not shown). The first body piece 2d and the second body piece 2e are each provided with a first bore 3i and a second bore 5i. The bores 3i, 5i are through bores that extends perpendicularly through the bodies of the first body piece 2d and the second body piece 2e. The first body piece 2d and the second body piece 2e are aligned such that the first bores 3i and the second bores 5i are coaxial, respectively. To assemble the fluid module 2, the first bore 3i in the first body piece 2d is fitted with the socket 3j and a gasket 10c, 10d at each end thereof. The first tube 3a is fitted inside the socket 3j. The second bore 5i in the first body piece 2d is fitted with a gasket 10a and the second tube 5a. The bores 3i, 5i of the second body piece 2e are fitted over the respective first tube 3a and second tube 5a. A gasket 10e is fitted inside the first bore 3i, and the product line (not shown) is secured to the fluid module 2 with the first bond 8. Another gasket 10b is fitted inside the second bore 5i, and the drain line (not shown) is secured to the fluid module 2 with a first tube 3a with the second bond 9.

Figure 15:
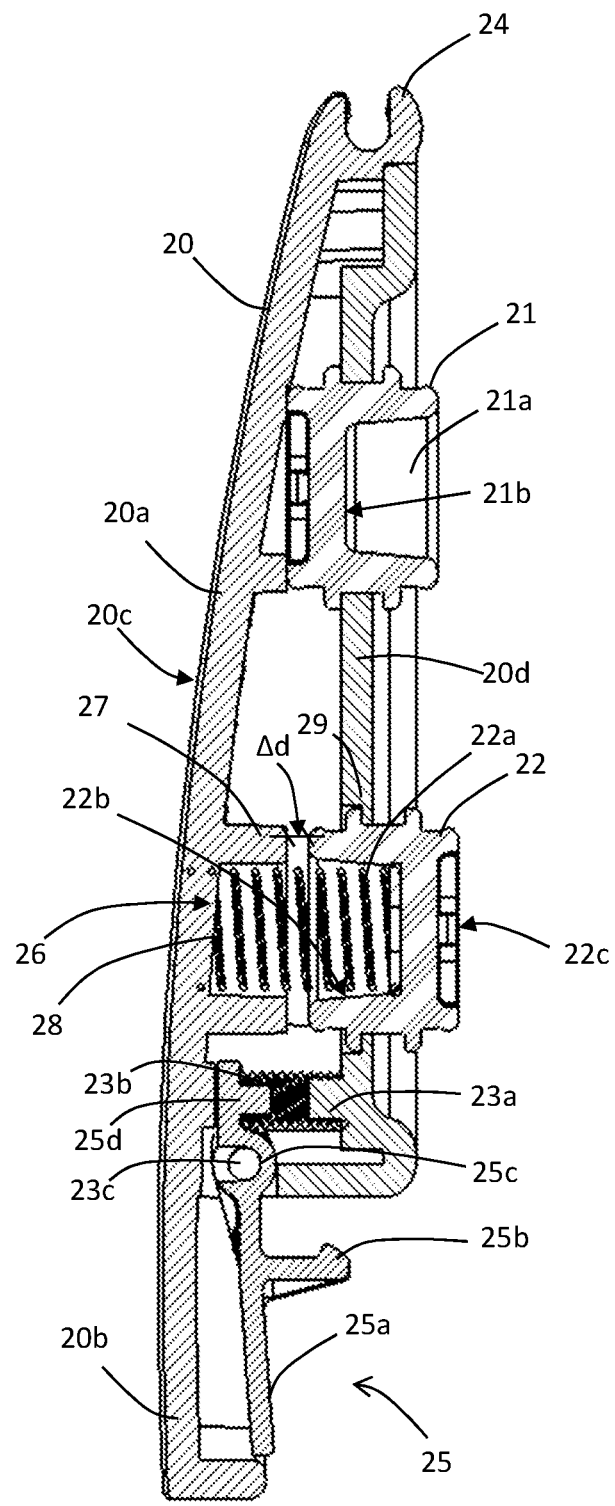
FIG. 15 illustrates a horizontal cross section in the plane C-C of the door in FIG. 9.

FIG. 15 illustrates cross-sectional view of the door 20 in FIG. 9 along a plane depicted by C-C. The door 20 is used for sealing the cleaning/disinfection loop and for protecting the ports 3, 5 when not in use. The seals 21, 22 of the door 20 may be silicon seals. The seals 21, 22 seal the flow block during disinfection. As shown in the figures, the seals 21, 22 may be the same kind of seal but oppositely arranged. Generally, a seal 21, 22 comprises a cylinder shaped body with two oppositely arranged surfaces. One side of the body is provided with a first rim encircling and perpendicularly extending from a first of the surfaces, i.e. an irregular surface, and the opposite side is provided with a second rim encircling and perpendicularly extending from a second of the surfaces. The second rim and the second surface delimit a space 21a. The second rim has a larger perpendicular extension that the first rim. The body is provided with two outer flanges that holds the seal 21, 22 to the inner wall 20d of the door 20. The outer flanges may be circumferential around the outer surface of the body. One of the outer flanges will also, when the door is in the closed position, debut against a seat 3d, 5d as has been previously explained.

The door 20 comprises a front side 20c and an opposite inner wall 20d. The first seal 21 and the second seal 22 are arranged to the inner wall 20d. The inner wall 20d defines an axis that in the closed position is parallel with the end faces 3f, 5f of the tubes 3a, 5a, and parallel with the outer faces or ends of the seats 3d, 5d.

The door 20 further comprises a spring-loaded latch assembly 25 for locking the door 20 to the fluid module 2, during cleaning/disinfection and protecting the ports 3, 5 when not in use. The latch is spring loaded to get a distinct and safe locking. When closing the door 20 the latch gives a distinct click sound when it is locked. The seals 21, 22 are positioned such that the seals will be in the correct position against the ports 3, 5 by support from the outer side of the door 20 and a minor compression of the silicon rubber seals 21, 22 approximately 0.5 mm, when the door 20 is closed against the fluid module 2.

The latch assembly 25 comprises a lever 25a, a spring 23b, a door spring seat 23a and a pin 23c. The lever 25a comprises a hook 25b arranged perpendicular to the main extension of the lever 25a, a pin passage 25c arranged with the pin 23c in the passage 25c or hole acting as a pivot point for the lever 25a, a spring seat 25d holding a spring 23b against a spring seat 23a of the door 20, arranged to the inner wall 20d. A spring force of the spring 23b maintains the hook 25b against the fluid module 2 when the door 20 is in the closed position. By pivoting the lever 25a against the door 20, the spring 23b is compressed and the hook 25b is withdrawn from the fluid module 2 and the door 20 can be opened. The lever 25*a* extends along an inner side of the second body part 20*b*.

The door 20 further comprises an additional spring arrangement 26. The additional spring arrangement 26 assures that when the door 20 is not locked, the door 20 will be distanced from the fluid module 2 such that the sensor arrangement 50 will not detect the presence of the door 20 and erroneously report that the door 20 is closed. This spring arrangement 26 comprises a spring 28 arranged between a spring seat 27 of the door 20 and the second seal 22. The spring 28 is provided in a space 22*a* of the second seal 22, delimited by an inner side 22*b* of a rim of the second seal 22. The second seal 22 is being biased by the spring 28 against an incision 29 of an inner side of the inner wall 20*d* of the door 20 with a flange of the second seal 22, with a predetermined spring force. The incision 29 may be circumferential around the second seal 22. The second seal 22 is being movable a distance Δd against the spring seat 27 by overcoming the spring force. Thus, when the door 20 is closed, the second seal 22 will rest against the second seat 5*d* and be pushed against the spring seat 27 such that the distance Δd is decreased. The distance Δd may be between 2 and 5 mm, e.g. 3 mm. Thus, the spring 28 opens the door 20 approximately 3 mm. This is enough for the door sensor arrangement 50 to loose the signal from the magnet in the door 20. The magnet is provided in the second body part 20*a*. A gasket may be provided to reduce the wear from the spring end against the second seal 22.

The seals 21, 22 have two different sides to be able to fulfill both sealing criteria with the same part. The first port 3, i.e. a product water port or purified water port, needs high flow volume to clean efficient and the second port 5, i.e. a drain port, needs higher flow speed to reduce the remaining fluid after disinfection. The first seal 21 and/or the second seal 22 may be arranged with an irregular outer surface 22*c*. An irregular surface may promote distribution of fluid, which promotes a complete cleaning of the port arrangement 1. The irregular outer surface 22*c* comprises one or several recesses, e.g. a recess shaped as a cross as shown e.g. in FIG. 3. The recessed cross essentially covers the outer surface 22*c* of the second seal 22. The second seal 22 is provided with a rim circumferential about the irregular outer surface 22*c*. The rim extends perpendicularly from the outer surface 22*c*, and mates with the seat 5*d*. The first seal 21 is also provided with a circumferential rim mating with the seat 3*d*. The rim encircles an interior surface 21*b* and a space 21*a* in the first seal 21. The space 21*a* gives room for fluid such that a larger flow of cleaning fluid can be accommodated.

The disclosure also relates to a method for performing port cleaning of a water producing apparatus, e.g. the water producing apparatus 100 that has been previously explained.

The method may be implemented as a computer program comprising instructions which, when the program is executed by the control unit 112, cause the control unit 112 and the thereto associated water producing apparatus 100 to carry out the method. The disclosure further relates to a computer-readable medium comprising instruction which, when executed by the control unit 112, cause the control unit 112 and the thereto associated water producing apparatus 100 to carry out the method.

Figure 16:
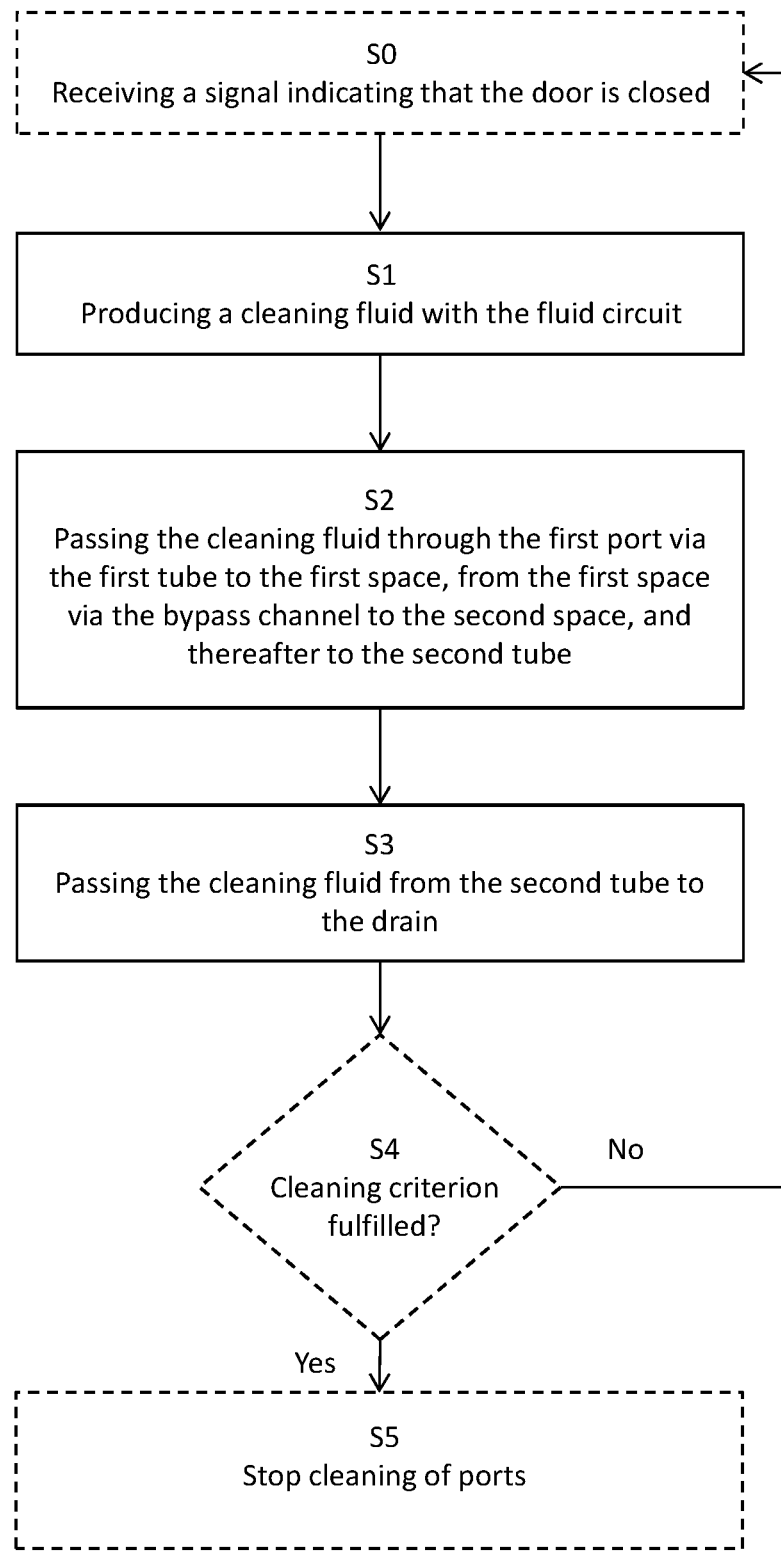
FIG. 16 illustrates a flow chart of a method for cleaning of a port arrangement.

The method will now be explained with reference to the flow chart of FIG. 16. As a first step, the method may comprise receiving S0 a door position signal indicating that the door 20 is closed. The method further comprises producing S1, or rather causing the fluid circuit (e.g. the fluid circuit 103) to produce, a cleaning fluid. The cleaning fluid may be purified water, heated purified water, purified water with a cleaning agent or heated purified water with a cleaning agent. The cleaning agent may be citric acid or derivatives thereof. The cleaning agent may be added to the fluid circuit via a cleaning agent port (not shown) connected to the fluid circuit. Thus, the producing S1 may comprise producing a heated cleaning fluid. With reference to the previously explained fluid module 2, the method further comprises passing S2 the cleaning fluid (thus controlling the cleaning fluid to flow) through the first port 3 via the first tube 3*a* to the first circumferential space 3*c*, from the first circumferential space 3*c* via the bypass channel 7 to the second circumferential space 5*c*, and thereafter to the second tube 5*a*. In other words, the cleaning fluid is directed or controlled to flow through the product line 108 by pumping with the pump P and controlling appropriate valve such as the valve device 107 in order to direct the cleaning fluid in the desired direction. The method further comprises passing S3 the cleaning fluid from the second tube 5*a* to the drain, e.g. via the drain line 109. In an exemplary embodiment, the passing S2 comprises passing the cleaning fluid during a certain time period meeting a cleaning criterion for the first port 3 and the second port 5. The cleaning criterion may include temperature and/or time duration for the cleaning. In a further step S4, the method comprises checking whether a cleaning criterion has been fulfilled. If the cleaning criterion has not been fulfilled, the method returns to step S0 or S1. The port cleaning continues until the cleaning criterion has been fulfilled. If the cleaning criterion has been fulfilled, the cleaning of the ports is stopped S5, and the production of cleaning fluid is stopped.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. A method for performing port cleaning of an apparatus having a casing, a fluid circuit enclosed inside the casing, and a port arrangement, the fluid circuit being arranged to produce a flow of purified water from a source of water and transport used fluid to a drain, wherein the port arrangement includes a first port, a second port, and a door, the port arrangement being positioned with respect to the casing such that the door, a front end of the first port, and a front end of the second port are each accessible from outside of the apparatus such that the first port is arranged to receive a first connector and the second port is arranged to receive a second connector, and wherein a back end of the first port is fluidly connected to the fluid circuit and a back end of the second port is fluidly connected to the fluid circuit, the method comprising:

producing a cleaning fluid with the fluid circuit;

passing the cleaning fluid through the first port via a first tube of the first port to a first circumferential space, from the first circumferential space via a bypass channel to a second circumferential space, and thereafter to a second tube of the second port; and passing the cleaning fluid from the second tube to the drain.

2. The method according to claim 1, further comprising passing the cleaning fluid during a certain time period meeting a cleaning criterion for the first port and the second port.

3. The method according to claim 1, further comprising receiving a signal indicating that the door is closed prior to passing the cleaning fluid through the first port.

4. The method according to claim 1, wherein a heated cleaning fluid is produced.

5. The method according to claim 1, wherein the bypass channel connects to the first circumferential space at an inner bottom of the first circumferential space, and the bypass channel connects to the second circumferential space at an inner bottom of the second circumferential space.

6. The method according to claim 5, wherein the bypass channel includes a main bore, wherein the main bore connects the first circumferential space and the second circumferential space.

7. A purified water producing apparatus comprising:
   a casing;
   a fluid circuit enclosed inside the casing, wherein the fluid circuit is arranged to produce a flow of purified water from a source of water and to transport used fluid to a drain; and
   a port arrangement including a first port, a second port, and a door, the port arrangement being positioned with respect to the casing such that the door, a front end of the first port and a front end of the second port are each accessible from outside of the purified water producing apparatus such that the first port is arranged to receive a first connector and the second port is arranged to receive a second connector,
   wherein a back end of the first port is fluidly connected to the fluid circuit and a back end of the second port is fluidly connected to the fluid circuit.

8. The purified water producing apparatus according to claim 7, further comprising a control unit configured to:
   receive a door position signal indicating a position of the door, and
   control a flow of cleaning fluid to the port arrangement based on the position of the door.

9. The purified water producing apparatus according to claim 8, wherein the control unit is configured to direct the flow of cleaning fluid to the back end of the first port upon the door position signal indicating that the door is in a closed position, whereby the cleaning fluid enters a first tube and flows into a first space of the first port, thereafter via a bypass channel to a second space and into a second tube, thereafter leaving the second port via the back end of the second port, and thereafter the cleaning fluid is further transported to the drain via the fluid circuit.

10. The purified water producing apparatus according to claim 9, wherein the second tube includes a threaded outer side.

11. The purified water producing apparatus according to claim 8, wherein the fluid circuit includes a heating device arranged to heat the cleaning fluid to a temperature meeting a cleaning criterion for the first port and the second port.

12. The purified water producing apparatus according to claim 7, wherein the first port and the second port are designed as Luer type conical fittings.

13. The purified water producing apparatus according to claim 7, further comprising a sensor arrangement configured to detect whether the door is in a closed position, and to generate a door position signal indicating a position of the door.

14. The purified water producing apparatus according to claim 7, further comprising a spring-loaded latch assembly configured to lock the door to the casing.

15. A non-transitory, computer-readable medium storing instructions that, when executed by a processor of an apparatus, cause the processor to perform a set of operations, the apparatus including a casing, a fluid circuit enclosed inside the casing, and a port arrangement, the fluid circuit being arranged to produce a flow of purified water from a source of water and to transport used fluid to a drain,
   wherein the port arrangement includes a first port, a second port, and a door, the port arrangement being positioned with respect to the casing such that the door, a front end of the first port and a front end of the second port are each accessible from outside of the apparatus such that the first port is arranged to receive a first connector and the second port is arranged to receive a second connector, and
   wherein a back end of the first port is fluidly connected to the fluid circuit and a back end of the second port is fluidly connected to the fluid circuit, the set of operations comprising:
   producing a cleaning fluid with the fluid circuit;
   passing the cleaning fluid through the first port via a first tube of the first port to a first circumferential space, from the first circumferential space via a bypass channel to a second circumferential space, and thereafter to a second tube of the second port; and
   passing the cleaning fluid from the second tube to the drain.

* * * * *